United States Patent [19]

Klausz

[11] Patent Number: 4,458,358

[45] Date of Patent: Jul. 3, 1984

[54] REFERENCE DETECTOR DEVICE FOR A MULTIDETECTOR TOMODENSITOMETER AND TOMODENSITOMETER COMPRISING SUCH A DEVICE

[75] Inventor: Remy Klausz, Paris, France

[73] Assignee: Thomson-CSF, Paris, France

[21] Appl. No.: 451,799

[22] Filed: Dec. 21, 1982

[30] Foreign Application Priority Data

Jan. 8, 1982 [FR] France .................. 82 00237

[51] Int. Cl.$^3$ .............................................. A61B 6/00
[52] U.S. Cl. ...................................... 378/19; 364/414; 378/18
[58] Field of Search ..................... 378/19, 18, 156, 16, 378/901; 364/414

[56] References Cited

U.S. PATENT DOCUMENTS 3,919,552 11/1975 Hounsfield ............................ 378/18
3,940,625 2/1976 Hounsfield .......................... 378/901
4,124,799 11/1978 Schittenhelm ....................... 378/18

FOREIGN PATENT DOCUMENTS 2019365 7/1970 France .
2249517 5/1975 France .
2335854 7/1977 France .
2348485 11/1977 France .
2353865 12/1977 France .

Primary Examiner—Alfred E. Smith
Assistant Examiner—T. N. Grigsby
Attorney, Agent, or Firm—Cushman, Darby & Cushman

[57] ABSTRACT

A reference detector device for a multidetector tomodensitometer comprises several reference detectors. It also comprises filters reproducing the most current objects as regards X-ray attenuation. Each reference detector is associated with one of the filters. A reference value, at a given instant, is obtained by a combination of the values detected at the same instant on different reference detectors.

15 Claims, 3 Drawing Figures

REFERENCE DETECTOR DEVICE FOR A MULTIDETECTOR TOMODENSITOMETER AND TOMODENSITOMETER COMPRISING SUCH A DEVICE

The present invention relates to a reference detector device for a multidetector tomodensitometer.

BACKGROUND OF THE INVENTION

Published German patent application No. 2,426,343 describes an apparatus in which the rotary anode radiogenerator tube supplies a wide beam of small thickness in the form of a sector or a fan, for the simultaneous irradiation through a complete section of the body which is to be examined, of several measuring detectors which are aligned and placed side by side. In this apparatus, several reference detectors of little bulk such as semiconductor diodes, are situated at the level of the inlet of the collimator which renders it possible to define the sector-shaped beam. The signals from these detectors are combined in a calculator circuit in order to determine the intensity of the radiation provided by the tube at each point of the beam and to compensate the overall and localised variations in the region of each measuring detector.

A second prior art device is that of published French Pat. No. 2,235,854 which describes an axial tomography apparatus comprising a reference detector intended to measure the intensity of the radiation supplied by an X-ray tube, a beam which irradiates the body which is to be examined, and through the latter, a measuring detector intended to measure the intensity of the radiation downstream of the body or member which is to be examined, the ratio between the signals delivered respectively by the measuring detectors and the reference detectors corresponding to the absorption of the radiation by this body. This reference detector comprises a scintillator af low absorption as regards X-rays, of which the absorption of the X-rays passing through the same is lower than 10 per 100, of which the absorption of the visible light emitted by itself is negligible, and which is arranged in such manner as to intercept the beam as a whole. The beam reaching the reference detector encompasses the whole of the useful beam reaching the measuring detector and is centred on this beam, the surface of the reference detector irradiated by the reference beam being at least equal to that of the measuring detector illuminated by the useful beam. The aperture of the beam reaching the reference detector is selected to be, for example, 10 to 20 times greater than that of the useful beam so as to obtain at the output side of this reference detector, a reference signal which has a level comparable to that of the measuring detector and of which the intensity variations due to the alternate heating and to its instability, to the rotation and faults of the surface of the anode as well as to the vibrations of this latter, are sufficiently close to those of the useful beam to compensate these in a very satisfactory manner, which is not so in the case of the devices which utilise as a reference an X-ray beam which does not encompass the whole of the useful beam as in the aforesaid prior art (point detectors), since the radiation diagram may equally vary with the rotation.

The first document mentioned makes it possible to compensate for an intensity variation as a function of the direction of the sector-like beam of the measuring detector in question.

The second document mentioned makes it possible to take into consideration the whole of the useful beam.

These devices make it possible to compensate for a variation of the quality of the beam related, for example, to the high voltage applied to the X-ray tube, but do not allow for the fact that the objects which are to be analysed are not uniform. The reference detector device of the invention makes it possible to mitigate this disadvantage by associating with the reference detectors compensating filters reproducing the most current objects from the point of view of X-ray attenuation.

SUMMARY OF THE INVENTION

The object of the invention is to provide a reference detector device for a multidetector tomodensitometer, said device comprising, in order to obtain at any point of a section of an object the measurement of the radiological density of said object, a source of X-rays and measuring detectors, characterised in that it also comprises plural reference detectors, filtering means which make it possible to obtain on each of the reference detectors a beam measurement in spectral conditions reproducing the attenuation of these X-rays by current objects which are to be analysed, each of the reference detectors being associated with one of these filtering means measuring the incident X radiation after attenuation by the said associated filtering means; means for instantaneously combining values encountered on the different reference detectors whilst making allowance for the values of the measurement at the point of measurement considered; and means for generating a reference signal value derived from this combination of values.

The invention also provides a tomodensitometer comprising a device of this nature.

BRIEF DESCRIPTION OF THE DRAWINGS

The invention will now be further described, by way of example, with reference to the accompanying drawings, in which.

DESCRIPTION OF THE PREFERRED EMBODIMENT

Figure 1:
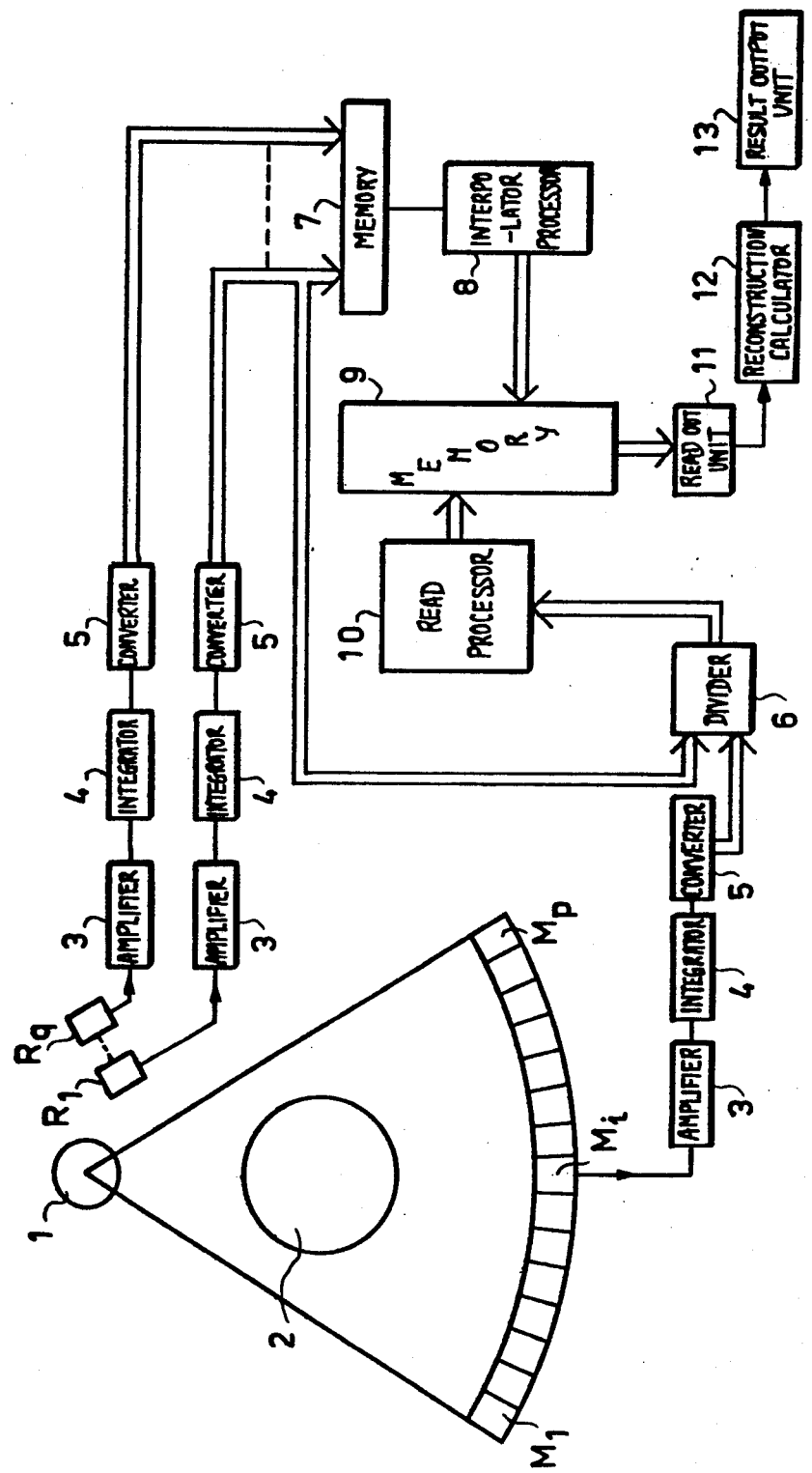
FIG. 1 illustrates one embodiment of a tomodensitometer comprising a reference detector device according to the invention.

The purpose of tomodensitometry is to exploit the variations of X-ray absorption by a body in an attempt to identify its nature or possible alterations in its nature. Combined with an image reconstruction process, it makes it possible to illustrate anatomical structures, for example by plotting an absorption chart.

Now, any process of physical measurement requires an interaction between the measuring instrument and the quantity measured.

As regards the laws governing the interaction of X-rays with materials: only absorption pemits to draw an appreciable energy from the beam. Any measurement of X-rays consequently requires an absorption of these X-rays.

The law of absorption is well known in the case of strictly monoenergetic X-rays; a partial absorption may consequently be acceptable if the precision problems linked with the number of particles measured are ignored.

On the contrary, in the case of a polyenergetic radiation, and if the beam spectrum composition is not known precisely, it is essential for the absorption to be total; it is thus possible to measure either the total number of photons notwithstanding their energy, or the total energy of the beam.

This condition imposing total absorption makes is mandatory to have a detector of which either the atomic number and the specific weight, or the length in the direction of the beam, are sufficient for the maximum possible energy of the radiation which is to be detected. Given the exponential nature of the absorption, it can never be strictly total; on the contrary, it is possible to approximate the same as closely as needed for the precision required.

In particular cases, it may equally be necessary to impose minimum dimensions on the section normal to the beam, so as to allow for the diffused X photons.

The mechanism of the detection as such derives directly from the absorption mechanism.

In principle, the quantity measured is the total linear attenuation coefficient $\mu$, but given the approximations performed, it is preferably replaced by the concept of radiologic density, these two quantities varying in the same direction. In particular, for a monochromatic radiation, they are equal, or there is at least a linear relationship between them. In practice it is frequently possible to equate the one to the other.

The primary element of a tomodensitometer is the radiogenerator device, comprising a high tension generator and a tube. The radiation emitted by the focus passes through the object to be measured and reaches the detector in which it is wholly absorbed; let I be the intensity of this radiation. The measurement of I is not sufficient to establish the characteristics of the absorbing body; as a matter of fact, it is necessary also to ascertain the intensity $I_o$ of the radiation emitted by the source. Assuming the monochromatic mode, then:

$$I = I_o e^{-\int \mu(x)dx}$$

$$\text{Log } I = \text{Log } (I_o e^{-\int \mu(x)dx})$$

$$\text{Log } I = \text{Log } I_o - \int \mu(x)dx$$

In the case of a length L of an homogenous body:

$$\text{Log } I_o - \text{Log } I = \mu L$$

$$\mu = (1/L)(\text{Log } I_o - \text{Log } I)$$

$$\mu = (1/L)(\text{Log } I_o/I)$$

The value $I_o$ may be measured under the same conditions as I, by simply withdrawing the absorbing body. Nevertheless, this method is inapplicable if it is wished to perform continuous measurements, except if the intensity X is sufficient stable to be measured once and for all.

By contrast, even for a beam coming from an X-ray tube, and if the high tension is constant, it may be acceptable to measure a part of the beam by means of a partial absorption detector situated in front of the object. A beam identical to the useful beam may equally be measured, but in another direction, subject to the condition that there are no variations in the spatial distribution of the transmission.

I and $I_o$ may be determined at the same time in this manner; the quantity permitting the calculation of $\mu$ actually being $I/I_o$ (or $I_o/I$), it is possible to refer to measurement in proportion.

The detector providing the measurement of $I_o$ is referred to as reference detector.

In the case of a polyenergetic distribution f(E), the intesity measured is the sum of the intensities relating to each energy:

$$I = \int f(E)dE = \int f_o(E)e^{-\int \mu(x,E)dx}dE$$

It is no longer possible to return to $\mu$ by applying the same calculations. In practice, the beam should be likened to a monochromatic beam, the use of a matching filter placed between the source and the object making it possible to minimise the error incurred, and it is sufficient to establish the difference between the Napierian logarithms of the measurements to determine a quantity equal to $\int \mu (x) dx$ (assuming the gains of the two channels to be balanced, in such a manner that $I = I_o$ if $\mu = 0$).

From the earliest descriptions of tomodensitometry, it is known that use may be made of a reference detector of this kind, having the task of measuring the X-ray flux which had not undergone attenuation, or a quantity proportional thereto.

As a rule, this detector is positioned close to the X-ray source; it may either be a total absorption detector situated outside the measuring beam, or a low-absorption detector positioned within the measuring beam which traverses the same before reaching the object measured.

The principal advantage of this second solution is that the reference detector perceives the source (focus of of the tube) under the same angle as the measurements, whereas the attenuation of the beam caused by the reference detector should remain weak, so that the flux utilised during the measurements remains sufficiently intensive. Given that in the case of X-rays it is impossible to produce an attenuator neutral with respect to energy, and that the source commonly utilised transmits a wide spectrum, there are two corollary disadvantages: a filtering action on the radiation by the reference detector, liable to affect the measurements (beam hardening), and reference measurements applicable to a spectrum different from that of the measurement flux.

These two filtering actions are complementary since the portion of the spectrum utilised for the reference measurement is precisely that which is not transmitted.

As a rule, the radiations of lesser energy are preferentially retained and measured by the reference detector.

The first solution, that is to say the utilisation of a total absorption reference detector is commonly more satisfactory, subject to the condition that the flux should not be different in the reference direction from that in the measurement direction, and that the detector should be as absorbing as the most absorbing object. A problem still persists however, connected with the polyenergetic nature of the flux transmitted by the source. As a matter of fact, there are no monochromatic radiations in nature, which entails a self-filtering action of the X-rays by the object, not all the wavelengths passing through a given line of this body in the same proportions. If a very thin object is considered, there is little inherent filtering action, but the longer wavelengths undergo absorption as the thickness of the body increases.

Considering the case of a homogenous circular object, the attenuation along a beam should depend only on the length travelled, which is small at the edges and large at the centre; nevertheless, the attenuation is not identical for all energies. The soft rays are extensively absorbed by a small length; the harder rays undergo a weak attenuation, even for a greater length; consequently, the object measured performs a filtering action on the radiation: the greater the length traversed, the more the radiation will harden, and the less will be the magnitude of its linear attenuation.

The attenuation coefficient consequently appears as being lower at the centre of the object than at its edges. After reconstruction, the radiologic density values calculated at the centre are consequently lower than that at the edges. A graphic illustration of the density in the object consequently has a hollow form, with raised edges; this is why the manifestation of this problem is referred to as "basin effect".

Given the exponential nature of this attenuation, the inherent filtering action is substantial primarily close to the edges. A substantial variation close to the edges, and a small variation at the centre, are consequently observed within the object.

In the case of a more complex shape, the action is particularly noticeable for the points situated on both the most highly absorbed radius and the least absorbed radius, as in the case of the frontal area of the head. Effects may then be observed which increase to the point that they prevent any utilisation of this area whilst masking a possible pathological condition. The problem becomes even more complex if this action is intensified by the presence of different substances. (As in the case of the bone of the cranial pan).

Endeavours are made to eliminate these shortcomings by a combination between high tension and filtration reducing the amplitude of the spectrum, and by specific correction means.

The flux undergoes a filtering action altering its quality, during traversal of the object measured. This action, known as "spectrum hardening", may be corrected in several ways, commonly based on application of calibration measurements. However, the calibration measurements are performed at a different instant from the instant of measurement, consequently they do not allow for possible variations of the quality of the beam, for example connected with variations of the high tension applied to the X-ray tube. These variations are manifested by a decalibrating action if they are slow, and by noise phenomenon on the measurements if their period of variation is comparable to the measurement sampling period or cycle; for example if a ratio of 2 or 3 prevails. As a matter of fact, the measurement conditions should evidently remain rigorously identical throughout, failing which the measurement variations between the start and finish of securing the readings are mistaken for density variations as a function of the angle of projection, and are manifested by false structures superimposed over the image, or "artefacts". Similarly, one should not forget that the tomodensitometer provides digital data. Now, the measurement concept implies that of fidelity, hence the need also for stability in the very long term (several months or years).

Finally, in the course of acquisition, each measurement corresponds to a sampling period of a few milliseconds. The experimental conditions should not fluctuate either on this scale.

This need applies both as regards the quality of the radiation utilised and to the position of the transmitter. By contrast, the circumstance of operation in a proportional manner makes it possible to eliminate the quantitative variations of the flux if they are not too substantial.

A voltage variation leads to: a modification of the efficiency of emission, a modification of the radiation damping spectrum, a modification of the excitation of the rays characteristic of the substance forming the anode of the tube.

All these variations are non-linear. As a rule, the detectors measure the total energy of the spectrum; the variation detected via a filter (beam filter or the object itself) consequently depends both on the variation of total energy transmitted and on the nature of the filtering action, in the form of the derivation of the energy distribution of the beam.

The modulation is thus comparatively small close to the maximum of the continuous spectrum, depending only on the overall efficiency variation; the modulation of the emission is total, close to the maximum energy.

The modulation as detected by the measuring detectors is the integral of the modulations for the spectrum as a whole. If the modulation detected by the reference detector is analogous to that detected by the measuring detectors, the calculation of the measurement/reference ratio is sufficient to eliminate the modulation.

However, the object not being uniform, this elimination cannot be performed in all cases as a rule, and an interference modulation remains. In order to eliminate this disadvantage, it is known that the modulation of the voltage applied to the tube may be rendered negligible and that the object may be rendered uniform by the utilisation of compensator filters. As a matter of fact, the passage lengths of the rays through the body are not equal, given for example the circular cross-section of the body and the cross-section of the material surrounding the same. For this reason, the detectors situated at the extreme positions tend to yield large output values even for a body of uniform absorption. To correct this fault, attenuator elements or filters of appropriate form are provided for the equalisation of the lengths of traversal.

Another solution is proposed in the device of the invention, consisting in utilising not one but several reference detectors measuring the incident flux after attenuation by filters reproducing the measured objects which are most current as regards radiation filtering. The value of a single reference measurement at a given instant may then be replaced by a combination of values discovered at the same instant on the different reference detectors.

The combination of reference detectors associated with filters may be established as a function of the kind of object which is measured, and is known in advance, and may vary as a function of the actual measurements or vary as a function of the result of a first reconstruction, in order to allow a second reconstruction of higher quality.

A particular attenuation of the X-rays corresponds to each filter. At a given instant, allowance is made for the composition of the value of the measurements at the point of measurement in question. Typical attenuations undergone by X-rays are then known, and recourse is then had to a combination of the reference detectors reproducing the attenuations of these types; as a matter of fact, the objects to be analysed are not homogenous, as a rule.

There are thus different simulation filters and thanks to an interpolation processor, it is possible to obtain the values equivalent to different thicknesses. These filters positioned in front of the reference detectors, make it possible to simulate the phenomenon. It is possible to come close to the actual case by interpolation. The filters may be of identical or dissimilar material making it possible to simulate the object.

The case of perspex sheets is usable for calibrating a rotary machine not during the measurement periods, by placing these in the beam instead of the object.

An embodiment of tomodensitometer according to the invention is illustrated in FIG. 1. An X-ray source 1 emits a beam of X-rays of which a part passes through the object 2 which is to be analysed before reaching a series of measuring detectors $M_1 \ldots M_p$. The reference detectors $R_1 \ldots R_q$ are illustrated as being outside the X-ray beam, but it is assumed in this case that they are reached by a part of the beam.

Whether for measurement or reference, the detectors are followed by an amplifier circuit 3, an integrator circuit 4 and a converter circuit 5 which enables analog/digital conversion but which may also perform the conversion into logarithms.

The intergrator circuit integrates the signal over a time period representing a predetermined degree of displacement of the X-ray source, in such a manner as to yield an analog signal representing the total intensity of the rays reaching the corresponding detector at this instant, and which is transmitted through the object 2 which is to be analysed along a trajectory actually examined by this detector, making allowance for the displacement of the X-ray source.

One of the reference detectors, for example the detector $R_1$, makes it possible to produce the measurement/reference value in the conventional sense, as a first approximation.

The reference signals $R_1$ and measurement signals $M_i$ are applied, once they have been processed, to the two corresponding input terminals of a divider circuit 6 producing a balanced signal corresponding to the ratio between the measurement signal and the reference signal. The division may be performed by substraction of the logarithms of the two signals.

The reference detector values obtained at a given instant make it possible to generate a set of reference values, with intermediate values established by interpolation. These values are collated in a table intended for reference purposes and are addressed as a function of the measurement value discovered, referenced in respect to a mean detector.

The reference detectors $R_1 \ldots R_q$ provide reference signals which after processing are stored in a memory 7. These values are then supplied for every sampling instant to an interpolator processor 8 which within a memory 9 generates the table of references as a function of the attenuation or better still directly generates the table of correspondence between measurements/reference (single reference) and measurements/references (polyenergetic reference).

The measurement/reference value obtained at the output of the divider circuit 6 serves the purpose of addressing the table via a read processor 10. The corrected value obtained at 11 is read out; these operations may be associated partially or totally with the calculation of the logarithms. The corrected value obtained at 11 is then applied for a reconstruction calculation performed at 12 to obtain a result at 13.

Each reference detector is associated with a filter which corresponds to a particular attenuation of the X-rays. This table may thus be completed at any instant, starting from the values obtained by the different reference detectors.

The kind of attenuation which should be taken into account, is thus known at a given instant for any measuring point. Consequently, it is possible to resort to a combination of reference detectors to allow for the fact that the object which is to be analysed is not generally homogenous.

The reference detectors may be positioned in the X-ray beam, but in a part of the beam which has not passed through the body which is to be analysed, which is always possible in tomodensitometry machines of the translatory kind, the analysis beams reaching the detectors which may be considered successively in time as measurement detectors or reference detectors since they emerge periodically from the field of the object. This is not true however for devices utilizing rotation only, and the process of the invention is then required.

Figure 2:
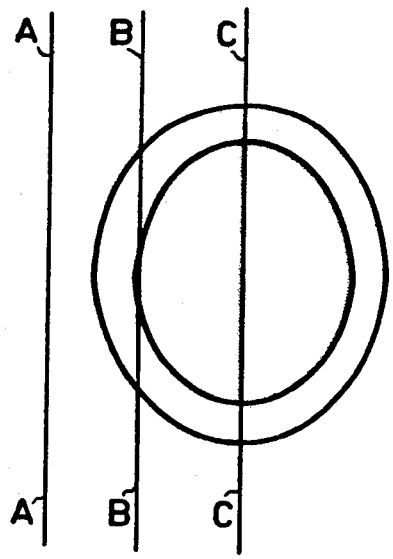
FIGS. 2 and 3 illustrate a particular feature of the device.
Figure 3:
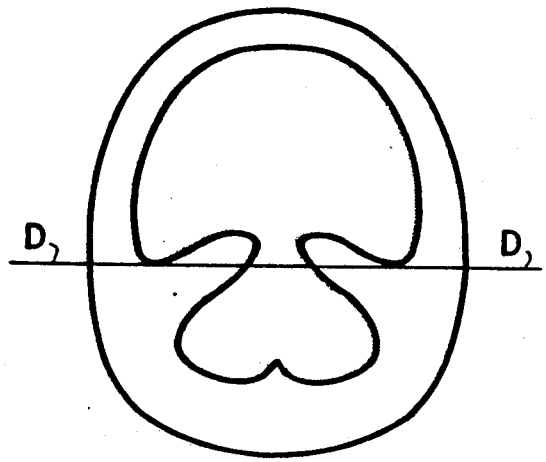

A correct simulation or compensation is not possible if an object is unknown. Allowance is made for an aggregation of all of the possible cases which are simulated at the primary level. As a function of the measurement performed at a secondary stage, corrections may be made which may be recurrent, it is possible to establish a feedback and to obtain a correct result in this manner, after stabilisation. Thus, taking as an example two axial section of the cranium, the one passing through the cerebral mass (FIG. 2) and the other through the base of the brain and the posterior fossa (FIG. 3), there is nothing but air along the axis A. Along the axis B, there is approximately 2.5 cms of bone of specific weight 1.6 which may be simulated by an aluminium sheet having a specific weight of 2.7. Along the axis C, there is approximately 1.5 cm of bone and 16 cms of tissue which may be simulated by a plastics material sheet comprising C, H, O components, for example by an epoxy resin. Along the major axis D, there are approximately 5 cms of bone and 10 cms of tissue.

Thus, these filters may thus be established, for example, by means of perspex sheets, thicknesses of water, sheets of polyester resin. At least one of the filters may for example contain a substance having a mean atomic number close to that of osseous structures, such as aluminium, a loaded resin or a material containing plaster or glass.

The reference detectors used may be of the conventional kind, that is to say of the scintillator type associated with a photomultiplier tube or of the gaseous ionisation detector type. The detector allotted to the reference measurement of the non-attenuated radiation should be as equivalent as possible in behaviour to the measuring detector, that is to say should be generally of the high efficiency type. The detectors corresponding to the different degrees of attenuation of the beam should measure the more energetic part of the beam and may be produced either by combining a total absorption detector with a filter, or by other methods such as, for example, application of a diffuser receiving the direct radiation and retransmitting by diffusion or fluorescence a radiation of lesser energy proportionately to the more energetic portion of the spectrum.

As a matter of fact, at the usual energy levels, the attenuation derives from three mechanisms: absorption by photoelectric effect, elastic diffusion (Thomson-Rayleigh effect), inelastic diffusion (Compton effect).

The inelastic diffusion effect (Compton effect) may be likened to an inelastic or uncushioned impact. The incident X photon arriving close to the cloud of electrons of an atom of the material traversed is deflected and loses energy which it imparts to electrons which it releases. The energy lost by the X photon is comparatively small; it varies with its angle of diffusion, being nil for nil deflection, and increasing with the size of the angle of deflection. Nevertheless, the probability of diffusion is a maximum for small angles and decreases with the energy.

However, given the considerable decrease of the photoelectric effect with the energy, the Compton effect is predominant for high levels of energy. It can be demonstrated that the Compton effect factor depends only on the electronic density of the absorbing body. This parameter varying little with the nature of the chemical elements, it may be assumed that the linear mass coefficient of the Compton effect is substantially identical for all bodies and consequently that the coefficient of linear attenuation by Compton effect is practically proportional to the specific weight of the absorbant.

The diffuser in question may be situated outside the useful portion of the X-ray beam. If a diffuser is situated within the beam, the reference detectors, as well as the filters associated with these, may be placed outside the useful beam whilst being reached by diffused X-rays.

This device of the invention permits instantaneous correction of the variations of the high tension controlling the X-ray source. It is also possible to correct phenomena of attenuation in translatory or rotary displacement.

I claim:

1. A reference detector device for a multidetector tomodensitometer, said device comprising, for the purpose of obtaining at any point of a section of an object the measurement of the radiologic density of said object, a source of X-rays and measuring detectors and said device also comprising a plurality of reference detectors, filtering means whereby it is possible to obtain at each of the reference detectors a beam measurement in spectral conditions reproducing the attenuation of these X-rays by current objects which are to be analysed, each of the reference detectors being associated with one of said filtering means, means for measuring the incident X-radiation after attenuation by the said associated filtering means; means for instantaneously combining values found at the different reference detectors whilst making allowance for the value of the measurements at the measurement point in question; and means for generating a reference signal value derived from this combination of values.

2. A detector device according to claim 1, in which the means of instantaneously combining the values detected at the different reference detectors enable, following a first conventional construction, to perform a second reconstruction with reference values improved whilst taking account of the values of measurements at the measuring point in question.

3. A detector device according to claim 1, in which the X-ray source projects a principal beam subdivided into two subsidiary beams separate from each other, only the first subsidiary beam striking the object and the second beam not striking the object, the reference detectors are total absorption detectors of the incident X-rays situated within the second subsidiary beam emerging from the X-ray source.

4. A detector device according to claim 1, in which an X-ray diffuser element is situated within the principal beam emerging from the X-ray source which is subdivided into two subsidiary beams independent of each other, only the first subsidiary beam striking the object, the reference detectors being situated outside the principal beam and on the trajectory of the diffused X-rays.

5. A detector device according to claim 4, in which the diffuser element is situated within the second subsidiary beam coming from the X-ray source.

6. A detector device according to claim 1, in which the reference detectors are detectors for partial absorption of incident X-rays and they are positioned within the principal beam emerging from the X-ray source.

7. A detector device according to claim 1, in which the filtering means utilised are perspex sheets.

8. A detector device according to claim 1, in which the filtering means utilised are produced by thicknesses of water.

9. A detector device according to claim 1, in which the filtering means utilised are sheets of polyester resin.

10. A detector device according to claim 1, in which at least one of the filtering means contains a material having a mean atomic number close to that of bony structures.

11. A detector device according to claim 10, in which this material is aluminium.

12. A detector device according to claim 10, in which this material is a loaded resin.

13. A detector device according to claim 10, in which this material comprises plaster.

14. A detector device according to claim 10, in which this material comprises glass.

15. A multidetector tomodensitometer, comprising a detector device according to claim 1.

* * * * *